(12) United States Patent
Lorenzini et al.

(10) Patent No.: US 6,803,485 B2
(45) Date of Patent: *Oct. 12, 2004

(54) PROCESS FOR THE PREPARATION OF IOPAMIDOL

(75) Inventors: Richard A. Lorenzini, Antioch, IL (US); Ashok V. Bhatia, Libertyville, IL (US); Steven A. Chamberlin, Waukegan, IL (US); Keith A. Drengler, Lindenhurst, IL (US); John J. Hufnagel, Waukegan, IL (US); Xiu C. Wang, Green Oaks, IL (US)

(73) Assignee: Bracco Imaging S.p.A., Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/257,690

(22) Filed: Feb. 26, 1999

(65) Prior Publication Data

US 2001/0056206 A1 Dec. 27, 2001

(51) Int. Cl.$^7$ ............................................. C07C 233/05
(52) U.S. Cl. ..................... 564/153; 424/9.452
(58) Field of Search ........................ 564/153; 424/9.452

(56) References Cited

U.S. PATENT DOCUMENTS

| | | | |
|---|---|---|---|
| 4,001,323 A | 1/1977 | Felder et al. | |
| 4,352,788 A | 10/1982 | Felder et al. | |
| 4,396,598 A | 8/1983 | Lin | |
| 5,177,261 A | 1/1993 | McCarthy et al. | |
| 5,204,005 A | 4/1993 | Doran, III et al. | |
| 5,256,393 A | 10/1993 | McCarthy et al. | |
| 5,362,905 A | 11/1994 | Villa et al. | |
| 5,371,278 A | 12/1994 | McCarthy et al. | |
| 5,527,926 A | 6/1996 | Ranganathan et al. | |
| 5,550,287 A | 8/1996 | Cannata et al. | |

FOREIGN PATENT DOCUMENTS

| | | |
|---|---|---|
| EP | 0118347 | 9/1984 |
| EP | 0516050 | 12/1992 |
| GB | 2272218 | 5/1994 |
| WO | 9214539 | 9/1992 |
| WO | 9218464 | 10/1992 |
| WO | 9504031 | 2/1995 |

OTHER PUBLICATIONS

Anelli et al, Tetrahedron, vol. 53, No. 34, pp 11919–11928, 1997.*

Grainger & Dawson, "Low Osmolar Contrast Media: An Appraisal", *Clinical Radiology*, 42:1–5 (1990).

Pillai, et al., "Heterocyclic Nonionic X–ray Contrast Agents. 3. The Synthesis of 5-[4-(Hydroxymethyl)-2-oxo-3-oxazolidinyl]-2,4,6-triiodo-1,3-benzene-dicarboxamide Derivatives" *J. Org. Chem.*, 59:1344–1350 (1994).

"Iopamidol", *The Merck Index*, 11$^{th}$ Edition, 4943–4944 (1989).

Clerici et al., Mass Spectral Characterization of Iopamidol. Biomedical Mass Spectrometry. 1982, vol. 9, No. 6, pp. 257–265.

\* cited by examiner

*Primary Examiner*—Shailendra Kumar
(74) *Attorney, Agent, or Firm*—Kramer, Levin, Naftalis & Frankel LLP

(57) ABSTRACT

The present invention discloses a process for the preparation of pure non-ionic contrast agents. The invention also includes a method for purifying the non-ionic contrast agents.

26 Claims, No Drawings

PROCESS FOR THE PREPARATION OF IOPAMIDOL

TECHNICAL FIELD

The present invention relates to a process for the preparation of nonionic, water soluble compounds that are useful as contrast agents.

BACKGROUND OF THE INVENTION

The introduction in X-ray diagnosis of contrast media containing non-ionic iodinated compounds as opacifying agents represented a remarkable progress in the state of the technique, so far that, these media will eventually substitute the traditional iodinated ionic products (see Grainger and Dawson, Clinical Radiology, 1990, 42, 1–5). These nonionic compounds, such as, (S)-N,N'-bis[2-hydroxy-1-(hydroxy (methyl)ethyl-5-[(2-hydroxy-1-oxypropylamino]-2,4,6,-triiodo-1,3-benzenedicarboxamide (iopamidol) and 5-[acetyl(2,3-dihydroxypropyl)amino]-N,N'-bis[2,3-dihydroxypropyl]-2,4,6,-triiodo-1,3-benzenedicarboxamide (iohexol), are useful as contrast enhancing agents for X-ray, magnetic resonance imaging (MRI) and angiography. These compounds have a lower frequency of adverse reactions in patients, during intravenous injection, than many ionic contrast agents.

However, the synthetic processes and, particularly, the final purification of these products are complex and expensive. Neutral iodinated opacifying agents differ from ionic ones because they cannot be isolated and purified by precipitation from water due to their high solubility. Thus the following problems must be solved: the removal of ionic species, usually inorganic salts, from the final reaction mixture, the recovery of valuable reagents in excess and of water-soluble reaction media. A preferred technique to be performed (see for example, U.S. patents: U.S. Pat. Nos. 4,352,788 and 4,001,323) is the one based on the submission of operations such as:

preliminary removal of the solvent, extraction of the residual reaction medium, preferably with a chlorinated solvent, elution of the aqueous phase on a system of columns of cationic and anionic ion-exchange resins, concentration of the elute by evaporation, crystallization of the crude residue.

The drawbacks related to this type of process include: a) a requirement for large complex and expensive purification plants for ion-exchange resins; b) a large quantity of thermal energy is required for the concentration of the water employed; c) the concentration of extremely diluted solutions causes the corresponding concentration of trace impurities; and d) the final product is exposed to a long-lasting thermal treatment.

U.S. Pat. No. 4,001,323 (the '323 patent) describes a process for preparing iopamidol which involves a) reacting 5-amino-2,4,6-triiodoisophthalyl dichloride (ATIPA-CI) with 2(S)-acetoxypropionyl chloride to form an acetyl-amide intermediate; b) reacting the acetyl amide intermediate with serinol to provide acetyliopamidol; c) reacting the acetyliopamidol with an aqueous base, such as, sodium hydroxide to hydrolyze the ester and provide iopamidol. The product is then purified by ion exchange treatment, followed by recrystallization from ethanol.

U.S. Pat. No. 4,352,788 (the '788 patent) describes a process for preparing compounds similar to the compounds of the '323 patent. The principle difference is the compounds of the '788 patent are alkylated at the aromatic nitrogen atom. The products are isolated by counter-current extraction or by using exchange resins.

However, problems that exist with the process disclosed in the '323 and the '788 patents include a) the use of a hazardous solvent; b) the basic hydrolysis can induce racemization of the optically active compound and may produce material which does not meet the U.S.P. optical rotation specification for iopamidol.

U.S. Pat. No. 4,396,598 (the '598 patent) discloses a method for preparing N,N'-bis(2,3-dihydroxypropyl)-5-N-(2-hydroxyethyl)glycolamido-2,4,6-triiodoisophthalimide. This patent also discloses the preparation starting with ATIPA-CI. However in the '598 patent, the polyhydroxy product is purified via preparative liquid chromatography.

U.S. Pat. No. 5,550,287 discloses a method for purification of the contrast agents again using a column with a strong anionic resin followed by a column with a weak anionic resin.

U.S. Pat. No. 5,204,005 discloses the use of a reverse phase chromatographic process for purification of water soluble, non-ionic contrast medium compounds.

An object of the present invention is to provide and process to prepare contrast agents which do not racemize the product.

An object of the present invention is to provide and process which furnishes the product contrast agent having a specific rotation that meets the requirements of the U.S.P. specification.

An object of the present invention is to provide an efficient method for the purification of non-ionic water soluble contrast agents.

SUMMARY OF THE INVENTION

The present invention relates to an improved process for the manufacture and purification of contrast enhancing agents, such as, iopamidol and iohexol. The process converts 5-amino-2,4,6-triiodoisophthalyl dichloride (ATIPA-CI) to an isophthalyl-diamide, such as, for example, 5-amino-N,N'-bis(1,3-diacetoxy-2-propyl)-2,4,6-triiodoisophthalamide (tetraacetyl-diamide) in a single reaction vessel by first reacting the ATIPA-CI with 2 equivalents of a dihydroxy-amine such as, for example, serinol, (2-amino-1,3-dihydroxypropane), or another suitable dihydroxyamino compound, in the presence of triethylamine, followed by treatment with an acid anhydride in the presence of a catalytic amount of dimethylaminopyridine (DMAP), to form the tetraester-diamide. The tetraester-amide product is then treated with an 2(S)-alkanoyloxylated propionyl chloride to produce the pentaester of iopamidol. The pentaester is treated with a catalytic amount of hydrochloric acid in methanol to deacylate the ester and provide iopamidol. The crude product is treated with an acid scavenging resin to remove the acid and purified by passing through a bed of nonionic polymeric adsorbent resin to remove other impurities from the reaction. The final purification is performed by recrystallization from ethanol or a mixture of acetonitrile in ethanol to provide pure iopamidol.

DETAILED DESCRIPTION OF THE INVENTION

All patents, patent applications, and literature references cited in the specification are hereby incorporated by reference in their entirety. In the case of inconsistencies, the present disclosure, including definitions, will prevail.

The present invention relates to a process for the preparation of a polyhydroxy compound and salts and enantiomers thereof having formula I.

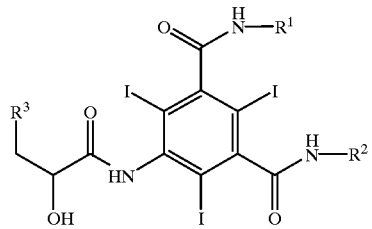

wherein R¹ and R² are dihydroxyalkyl groups, and R³ is hydrogen, alkyl, or hydroxy. The process comprising the step of deacylating an acylated compound having the formula:

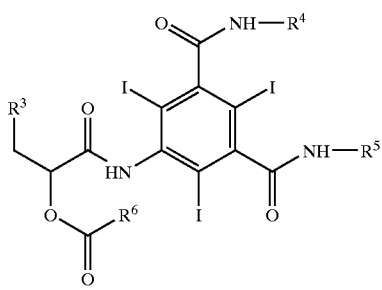

in an acidic medium, to provide the free polyhydroxy compound. R⁴ and R⁵ are optionally acylated dihydroxyalkyl groups and R⁶ is lower alkyl. The polyhydroxy compound can be purified by treatment with an acid scavenging resin.

The invention also contemplates compounds having the formula:

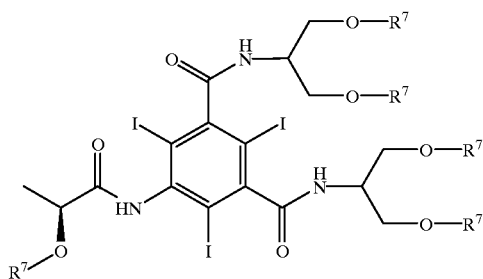

wherein each R⁷ is an acyl group, and salts and enantiomers thereof.

Examples of acyl groups include groups such as, for example, formyl, acetyl, propionyl, butanoyl, pivaloyl, pentanoyl, trifluoroacetyl, trichloroacetyl, benzoyl, and the like. The preferred acyl groups are formyl, acetyl, propionyl, and butanoyl. The most preferred acyl group is acetyl.

The dihydroxyalkyl groups are straight or branched chain alkyl radicals containing from 2 to 6 carbon atoms and having two hydroxy groups. Most preferred dihydroxyalkyl groups are 1,3-dihydroxypropyl, 1,2-dihydroxypropyl.

The lower alkyl groups include straight or branched chain alkyl groups having from 1 to about 6 carbon atoms. Examples of lower alkyl groups include groups such as, for example, methyl, ethyl, n-propyl, iso-propyl, 2-methylpropyl n-butyl, 2-butyl, t-butyl n-pentyl, 1-methylbutyl, 2,2-dimethylbutyl, 2-methylpentyl, 2,2-dimethylpropyl, and n-hexyl,. The preferred lower alkyl groups are methyl, ethyl, n-propyl, iso-propyl, n-butyl, and t-butyl. More preferred are methyl and ethyl. Most preferred is methyl.

The advantages of the present invention include reduction of racemization of the product and an improved method for isolation of the product. This provides a product with a higher enantiomeric excess (ee) than the methods disclosed in the documents discussed above. The process of the invention involves the deacylation of an ester of iopamidol using a catalytic amount of acid. The acid is removed by batch treatment with a small amount of an acid scavenging resin. Final purification involves passing an aqueous solution of the product through a column of non-ionic polymeric adsorbent resin, followed by concentration to an oil and recrystallization from acetonitrile/ethanol or ethanol alone. This process consistently produces material which meets all U.S.P. specifications including the optical rotation specification.

Typical acid scavenging resins include weak basic resins such as, for example, IRA-68, IRA-67, Dowex® WGR-2, and the like. These resins remove any acid present.

Typical nonionic polymeric adsorption resins include polyaromatic resins, such as, for example, Amberlite XAD-16, XAD-4, and the like. These resins function to remove impurities formed during the reaction process.

A preferred embodiment is illustrated in Scheme 1 below. The process converts 5-amino-2,4,6-triiodoisophthalyl dichloride (ATIPA-Cl) to 5-amino-N,N'-bis(1,3-diacetoxy-2-propyl)-2,4,6-triiodoisophthalamide (tetraacetyl-diamide) in a single reaction vessel by first reacting ATIPA-Cl with 2 equivalents of serinol in the presence of triethylamine followed by treatment with acetic anhydride in the presence of a catalytic amount of dimethylaminopyridine (DMAP). The tetraacetyl-diamide product is readily isolated by precipitation from water and further purification is generally not required. The tetraacetyl compound is treated with 2(S)-acetoxypropionyl chloride to provide a pentaacetyl-triamide. The acetate groups are removed by a transesterification reaction with hydrochloric acid in methanol to provide iopamidol. The acid is removed with an acid scavenging resin. Other impurities are removed using a polymer absorption resin. The product can be crystallized from ethanol or, optionally, if it contains excessive impurities, an acetonitrile/ethanol mixture.

SCHEME I

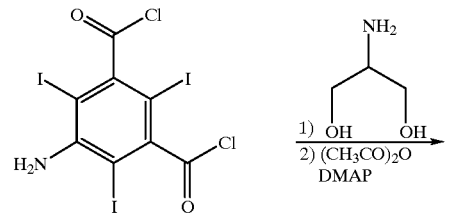

-continued

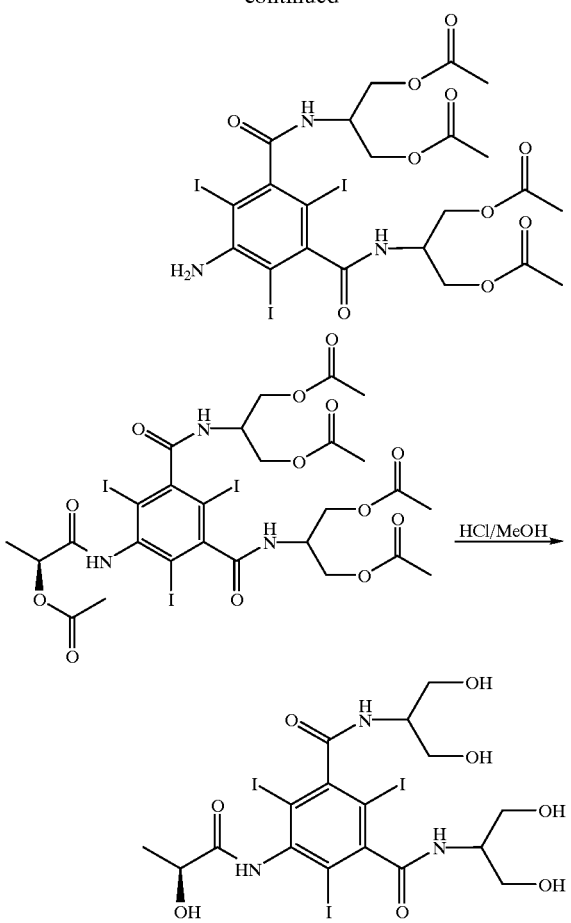

Preferred compounds of the invention include the compounds:

(S)-N,N'-bis[2-hydroxy-1-(hydroxy(methyl)ethyl]-5-[(2-hydroxy-1-oxypropylamino]-2,4,6,-triiodo-1,3-benzenedicarboxamide, (S)-N,N'-bis[2,3-dihydroxypropyl]-5-[(2-hydroxy-1-oxypropylamino]-2,4,6,-triiodo-1,3-benzenedicarboxamide, and 5-[acetyl(2,3-dihydroxypropyl)amino]-N,N'-bis[2,3-dihydroxypropyl]-2,4,6,-triiodo-1,3-benzenedicarboxamide, (iohexol).

The process of the invention includes a method for deacylating a compound wherein all of the hydroxy groups have been acylated and a method for deacylating monoacylated compounds such as, for example, acetyliopamidol. Examples of the alkanoyloxy group include acetyloxy, propionyloxy, butanoyloxy and the like. A preferred alkanoyloxy group is acetyloxy. The acyl groups include groups such as, for example, acetyl, propionyl, butanoyl and the like. A preferred acyl group is acetyl.

The invention also contemplates a method for the purification of water soluble nonionic contrast agents.

As used herein, the term "acyl" refers to groups having the formula —C(=O)—R$^{95}$ wherein R$^{95}$ is hydrogen or a lower alkyl or aryl group. Representative examples of acyl groups include groups such as, for example, formyl, acetyl, propionyl, and the like.

As used herein, the term "alkyl" refers to straight or branched chain alkyl radicals containing from 1 to 12 carbon atoms. The term "lower alkyl" refers to straight or branched chain alkyl radicals containing from 1 to 6 carbon atoms including, but not limited to, methyl, ethyl, n-propyl, iso-propyl, 2-methylpropyl n-butyl, 2-butyl, t-butyl n-pentyl, 1-methylbutyl, 2,2-dimethylbutyl, 2-methylpentyl, 2,2-dimethylpropyl, n-hexyl, and the like.

As used herein, the term "aryl" refers to a mono- or bicyclic carbocyclic ring system having one or two aromatic rings including, but not limited to, phenyl, naphthyl, tetrahydronaphthyl, indanyl, indenyl and the like. Aryl groups can be unsubstituted or substituted with one, two or three substituents.

As used herein, the term "dihydroxyalkyl" refers to straight or branched chain alkyl radicals containing from 2 to 6 carbon atoms and having two hydroxy groups. Representative examples of dihydroxyalkyl groups include groups such as, for example, 1,3-dihydroxypropyl, 1,2-dihydroxypropyl, and the like.

The term "halo" as used herein refers to F, Cl, Br or I.

The term "haloalkyl" as used herein refers to a lower alkyl group in which one or more hydrogen atoms has been replaced with a halogen including, but not limited to, trifluoromethyl, trichloromethyl, difuoromethyl, dichloromethyl, fluoromethyl, chloromethyl, chloroethyl, 2,2-dichloroethyl and the like.

As used herein, the terms "S" and "R" configuration are as defined by the IUPAC 1974 Recommendations for Section E, Fundamental Stereochemistry, Pure Appl. Chem. (1976) 45, 13–30.

The reagents required for the synthesis of the compounds of the invention are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA); Alfa Aesar (Ward Hill, Mass. 01835-9953); Eastman Chemical Company (Rochester, New York 14652-3512); Lancaster Synthesis Inc. (Windham, N.H. 03087-9977); Spectrum Chemical Manufacturing Corp. (Janssen Chemical) (New Brunswick, N.J. 08901); Pfaltz and Bauer (Waterbury, Conn. 06708). Compounds which are not commercially available can be prepared by employing known methods from the chemical literature.

The polymeric resins, e.g., IR-68 and Ambelite XAD-16 are available from suppliers such as Rohm and Haas Company (Philadelphia, Pa. 19106).

The following examples illustrate the process of the invention, without limitation.

EXAMPLE 1

N,N'-bis[2-(acetyloxy)-1-[(acetyloxy)methyl]ethyl]-5-amino-2,4,6-triiodo-1,3-benzenedicarboxamide.

A suitable reaction vessel was charged with 50 kg of 5-amino-2,4,6-triiodoisophthalyl dichloride (ATIPA-CI) and 75 kg dimethylacetamide (DMA) and mixed. A solution of 18.5 kg of 2-amino-1,3-propanediol (serinol) and 30 kg of triethylamine in 45 kg of DMA was added to the above vessel. The reaction was mixed while gradually elevating the temperature to about 30° C. This temperature was maintained for about 1.5 hours. The reaction was cooled and 0.5 kg of 4-dimethylaminopyridine was added to the vessel followed by the slow addition of 52 kg of acetic anhydride. The reaction was stirred for about 2 hours and quenched by slow addition to water. The solid was isolated by filtration, washed with water and dried (yield: 66 kg; 90%). $^1$H NMR (300 MHz, DMSO-d$_6$) δ 2.0 (S, 12H), 4.1(m, 8H), 4.3(m, 2H), 5.5 (S, 2H), 8.4, 8.7 (2d, 2H). $^{13}$C NMR (75 MHz, DMSO-d$_6$) δ 20.8, 46.9, 62.1, 73.5 79.7, 147.6, 148.5, 169.5, 170.2.

EXAMPLE 2
Preparation of Pentaacetyliopamidol

The product, 55 kg, prepared in Example 1, was dissolved in 60 kg of DMA. 2(S)-Acetoxypropionyl chloride, 20 kg, was added slowly. The reaction was stirred at room temperature for about 2 hours and quenched by the slow addition of isopropanol. The mixture was neutralized with tributylamine. The pentaacetyliopamidol is collected by filtration, washed with isopropanol and dried (yield: 56 kg, 90%). $^1$H NMR (300 Mz, DMSO-$d_6$) δ 1.5 (d, 3H), 2.0 (S, 12H), 2.1(2S,3H0, 4.1(m, 8H), 4.3(m, 2H), 5.2(q, 1H), 8.8 (d,1 H0, 8.9(t,1 H), 10.1(S, 1H). $^{13}$C NMR (75 MHz, DMSO-$d_6$) 17.6, 20.8, 47.0, 62.1, 69.4, 90.1, 99.0, 142.4, 149.6, 168.0, 169.1, 169.5, 170.3.

EXAMPLE 3
Preparation of Iopamidol

A solution of 58 kg of pentaacetyliopamidol in 400 L of methanol containing a catalytic amount, 400 g, of aqueous hydrochloric acid was heated at reflux for about 30 hours. The methanol was removed by distillation and the residue dissolved in water. The acid was neutralized by stirring the solution with an acid-scavenging resin (IRA-68). The resin was removed by filtration and the resulting aqueous solution was passed through a 50 kg column of amberlite XAD-16 resin. The eluant was concentrated to provide an oil and the residue crystallized by heating the oil in a mixture comprising 40 kg of acetonitrile and 150 L of ethanol, followed by cooling. The iopamidol was collected by filtration, washed with ethanol and dried (yield: 34 kg, 74%).

Specific Rotation $[\alpha]_D^{20}$=−5.0 in methanol. $^1$H NMR (300 MHz, $D_2O$)δ1.6(d, 3H), 3.8 (d,8H), 4.2(m, 2H), 4.5(q, 1H). 13C NMR (75 MHz, $D_2O$) δ 21.5, 55.1, 61.8, 70.2, 91.0, 99.8, 144.2, 151.2, 173.8, 178.6.

COMPARATIVE EXAMPLE 1
L-5-(α-Acetoxypropionylamino)2,4,6-triiodo-isophthalyl chloride A solution of 100 g (168 mmole) 5-amino-2.4.6-triiodo-isophthalyl chloride, in 100 ml of dimethylacetamide was prepared. L-2-Acetoxypropionyl chloride was added dropwise to the solution at room temperature. The mixture was stirred for 16 hours, at ambient temperature. The reaction mixture was diluted with 200 mL of acetone and added dropwise to 500 mL of cold water. The solid product was collected, washed with water and dried under vacuum at 65° C. (Yield: 110 g, 93%).

COMPARATIVE EXAMPLE 2
L-5-α-Acetoxypropionylamino-2,4,6-triiodo-isophthalic acid di-(1,3-dihydroxyisopropylamide) (acetyliopamidol)

The intermediate prepared in Example 1, (27.0 g 38.0 mmole), was dissolved in 140 ml dimethylacetamide. Tributylamine, (14.2 g, 76.6 mmole) was added followed by a solution of 1,3-dihydroxy (8.6 g, 94.4 mmole), in 80 mL of dimethylacetamide. The mixture was stirred and heated at 50 C. for 22 hours. The reaction mixture was added dropwise to 1.0 L of methylene chloride with vigorous agitation, and the resulting precipitate was filtered off and washed to provide 25.8 g of the title compound.

COMPARATIVE EXAMPLE 3
L-5-α-Hydroxypropionylamino-2,4,6-triiodo-isophthalic acid di-(1,3-dihydroxyisopropylamide) (iopamidol).

The L-5-α-acetoxypropionylamino-2,4,6,-triiodoisophthalic acid di-(1,3-dihydroxyisopropylamide) (20 g, 24.4 mmole) was dissolved in water. The pH was adjusted to 11 with concentrated sodium hydroxide solution and heated to 40 C. Additional NaOH solution was added until the pH stabilized, indicating the complete saponification of the acetoxy groups. The reaction mixture was acidified to pH 7 with 3N hydrochloric acid. The resultant solution passed over a column of IR 120 resin (25 g) and followed by passing over a column of A-21 (35 g) resin to desalt the solution. (Resins available from the Rohm & Haas Co.) The product was purified by passing over a XAD-16 column. The title compound was obtained by removal of the solvent in vacuo followed by crystallization from acetonitrile\water (1:3) (yield: 9.2 g; 48%).

Elemental analysis, calculated for $C_{17}H_{22}I_3N_3O_{11}$: C, 26.27%. and I, 47.79%. Found: C, 26.27% and I, 48.79%.

Specific Rotation $[\alpha]_D^{20}$=−4.5 in methanol.

The foregoing is merely illustrative of the invention and is not intended to limit the invention to the disclosed processes and reaction conditions. Variations which are obvious to one of ordinary skill in the art are intended to be included within the scope and nature of the invention which are defined in the appended claims.

What is claimed is:

1. A process for the preparation of a polyhydroxy compound, and salts and enantiomers thereof, having formula I:

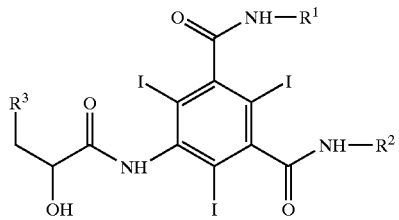

wherein $R^1$ and $R^2$ are dihydroxyalkyl and $R^3$ is hydrogen, alkyl, or hydroxyl;

said process comprising the step of deacylating an acylated compound having the formula:

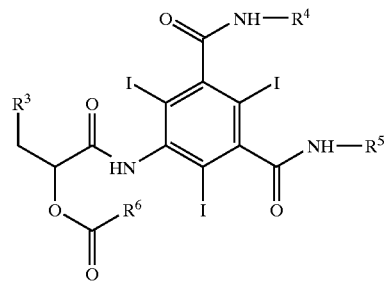

in an acid and alcohol medium, wherein $R^4$ and $R^5$ are acylated dihydroxyalkyl groups, and $R^6$ is lower alkyl.

2. The process according to claim 1 wherein $R^1$ and $R^2$ are independently selected from the group consisting of 1,3-dihydroxypropyl and 2,3-dihydroxypropyl.

3. The process according to claim 2 wherein $R^1$ and $R^2$ are 1,3-dihydroxypropyl.

4. The process according to claim 2 wherein $R^1$ and $R^2$ are 2,3-dihydroxypropyl.

5. The process according to claim 1 wherein the acylated dihydroxyalkyl group is acylated with an acyl group selected from the group consisting of formyl, acetyl, propionyl, and butanoyl.

6. The process according to claim 5 wherein the acylated dihydroxyalkyl group is acylated with an acyl group selected from the group consisting of acetyl, propionyl, and butanoyl.

7. The process according to any of claims 1 or 2–6, wherein $R^4$ and $R^5$ are 1,3-diacetyloxypropyl.

8. The process according to any of claims 1 or 2–6, wherein $R^4$ and $R^5$ are 2,3-diacetyloxypropyl.

9. The process according to claim 1, wherein $R^3$ is selected from the group consisting of hydrogen, methyl, ethyl, n-propyl, iso-propyl, n-butyl, iso-butyl, sec-butyl, and t-butyl.

10. The process according to claim 9, wherein $R^3$ is selected from the group consisting of hydrogen, methyl, ethyl, n-propyl, and iso-propyl.

11. The process according to claim 10, wherein $R^3$ is methyl.

12. The process according to claim 10, wherein $R^3$ is hydrogen.

13. The process according to claim 1, wherein $R^6$ is selected from the group consisting of methyl, ethyl, propyl, and butyl.

14. The process according to claim 13, wherein $R^6$ is selected from the group consisting of methyl, ethyl, n-propyl, iso-propyl, n-butyl, and t-butyl.

15. The process according to claim 14, wherein $R^6$ is selected from the group consisting of methyl and ethyl.

16. The process according to claim 15, wherein $R^6$ is methyl.

17. A process according to claim 1 wherein said alcohol of said acid and alcohol medium is methanol.

18. The process according to claim 1 wherein said acid medium is hydrochloric acid.

19. The process according to claim 1 wherein said acid and alcohol medium is hydrochloric acid in methanol.

20. The process according to claim 1 wherein said acid and alcohol medium is represented by a catalytic amount of hydrochloric acid in methanol.

21. The process according to claim 1 wherein the acylated dihydroxyalkyl group is acetyl dihydroxyalkyl and the deacylation step is a transesterification reaction.

22. The process according to claim 21 wherein the transesterification reaction is conducted with hydrochloric acid in methanol.

23. The process according to claim 21 wherein the transesterification reaction is conducted with a catalytic amount of hydrochloric acid in methanol.

24. A process for the preparation of iopamidol comprising subjecting pentaacetyliopamidol to a transesterification reaction in an acid and alcohol medium.

25. A process for the preparation of iopamidol comprising deacylating pentaacetyliopamidol in an acid and alcohol medium.

26. A process for the preparation of iopamidol comprising deacylating pentaacetyliopamidol in hydrochloric acid and methanol.

* * * * *